US012727763B2

(12) United States Patent
Subhash et al.

(10) Patent No.: US 12,727,763 B2
(45) Date of Patent: Sep. 8, 2026

(54) SYSTEM FOR DIAGNOSING ORAL CARE CONDITIONS AND REMEDIATING SAME, AND METHODS THEREOF

(71) Applicant: Colgate-Palmolive Company, New York, NY (US)

(72) Inventors: Hrebesh Molly Subhash, Somerset, NJ (US); Benny E. Urban, Jr., Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 255 days.

(21) Appl. No.: 18/549,840

(22) PCT Filed: Feb. 3, 2022

(86) PCT No.: PCT/US2022/015054
§ 371 (c)(1),
(2) Date: Sep. 8, 2023

(87) PCT Pub. No.: WO2022/197384
PCT Pub. Date: Sep. 22, 2022

(65) Prior Publication Data

US 2024/0180429 A1 Jun. 6, 2024

Related U.S. Application Data

(60) Provisional application No. 63/162,087, filed on Mar. 17, 2021.

(51) Int. Cl.
*A61B 5/00* (2006.01)
*A61C 19/06* (2006.01)

(52) U.S. Cl.
CPC .......... *A61B 5/0088* (2013.01); *A61B 5/0077* (2013.01); *A61B 5/6898* (2013.01); *A61B 5/7264* (2013.01); *A61C 19/063* (2013.01)

(58) Field of Classification Search
CPC ... A61B 5/0088; A61B 5/0077; A61B 5/6898; A61B 5/7264; A61B 5/4547;
(Continued)

(56) References Cited

U.S. PATENT DOCUMENTS

| | | | | |
|---|---|---|---|---|
| 5,236,971 A * | 8/1993 | Murray | B01F 21/20 | 433/201.1 |
| 6,212,425 B1 * | 4/2001 | Irion | A61B 5/0084 | 600/476 |

(Continued)

FOREIGN PATENT DOCUMENTS

| | | |
|---|---|---|
| CN | 106137123 | 11/2016 |
| JP | 2010526638 | 8/2010 |

(Continued)

OTHER PUBLICATIONS

Angelino et al., 2017, "Clinical validation and assessment of a modular flourescent imaging system and algorithm for rapid detection and quantification of dental plaque", BMC Oral Health, Biomed Central Ltd., vol. 17(1):1-10.

(Continued)

*Primary Examiner* — Ryan W Sherwin

(57) ABSTRACT

The present disclosure may be directed to a system including a diagnostic device configured to illuminate a portion of the oral cavity and detect information relating to emission fluorescence and/or back scattered light relating to the illuminated portion of the oral cavity. A processor may be configured to receive the information relating to the emission fluorescence and/or back scattered light; determine the oral condition of the oral cavity based on the received information relating to the emission fluorescence and/or back scattered light; determine ingredients that are expected to remedy the oral condition of the oral cavity; and cause identities of the ingredients to be transmitted. The product dispenser may receive the identities of the plurality of
(Continued)

ingredients; mix the identified plurality of ingredients within the mixing chamber; and dispense a product expected to remedy the oral condition of the oral cavity.

20 Claims, 12 Drawing Sheets

(58) Field of Classification Search
CPC ..... A61C 19/063; A61C 19/005; A61C 1/088; A61C 17/0202; A61C 17/0205; A61C 19/04; A46B 2200/1066; A46B 11/0058; A46B 11/0065; A46B 13/04; A46B 15/0034
See application file for complete search history.

(56) References Cited

U.S. PATENT DOCUMENTS 8,214,958 B2 7/2012 Pinyayev
9,138,041 B2 9/2015 Samain
9,789,295 B2 10/2017 Zhou
10,152,529 B2 12/2018 Hyde et al.
10,219,737 B2 3/2019 Ibrahim et al.
10,376,246 B2 8/2019 Kashyap et al.
10,878,063 B2 12/2020 Li et al.
10,888,201 B2 1/2021 Pai
2003/0194678 A1 10/2003 Viltro et al.
2004/0199227 A1* 10/2004 Altshuler ................. A61K 8/02 607/100
2008/0060148 A1* 3/2008 Pinyayev ............. A61B 5/0088 15/4
2010/0016669 A1* 1/2010 Takaoka ............. A61B 1/00009 600/160
2010/0036260 A1* 2/2010 Zuluaga ............... A61B 1/0684 600/249
2011/0151409 A1* 6/2011 Binner ................. G01N 21/645 600/431
2012/0021375 A1* 1/2012 Binner ................... A61B 5/097 433/89
2013/0096376 A1* 4/2013 Takei ................... A61B 1/0655 600/103
2015/0305626 A1* 10/2015 Deane .................. A61B 5/0071 433/216
2018/0184857 A1* 7/2018 Pai ......................... A46B 3/005
2019/0328234 A1 10/2019 Seibel
2020/0146794 A1 5/2020 Lee et al.

FOREIGN PATENT DOCUMENTS

WO 2019/210184 10/2019
WO 2022/197384 9/2022

OTHER PUBLICATIONS

International Search Report and the Written Opinion of the International Searching Authority issued in International Application PCT/US2022/015054 mailed May 16, 2022.

* cited by examiner 200
206
203
203
208
207
204

204
203
203
206
208

207
208
205
204
202
205
201

202a
202b
202c

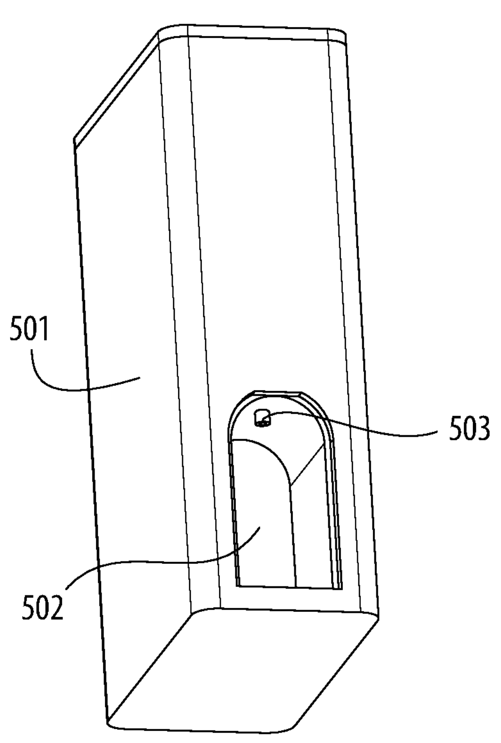
FIG. 5A
507d
507c
507c
503
507d
FIG. 5B
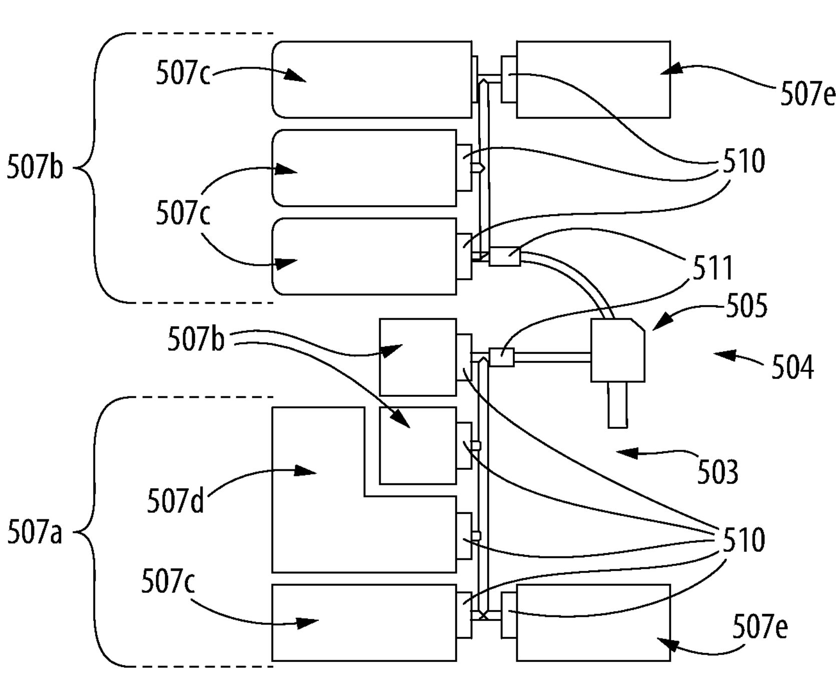
FIG. 5C 500
507e
504
588
503
502
586
510
507f
511
580
582
584

SYSTEM FOR DIAGNOSING ORAL CARE CONDITIONS AND REMEDIATING SAME, AND METHODS THEREOF

CROSS-REFERENCE TO RELATED APPLICATIONS

The present application claims priority to U.S. Provisional Patent Application Ser. No. 63/162,087, filed Mar. 17, 2021, the entirety of which is incorporated herein by reference.

BACKGROUND

Oral health problems can take many forms, such as tooth decay, tooth stain, tooth sensitivity, dry mouth, periodontal disease, caries, and bad breath. Periodontal disease and tooth caries are often caused by certain bacterial species in the mouth that interact with proteins present in saliva to form a film, known as plaque, that coats the teeth. If this biofilm build up progresses, the acid produced by the bacteria can attack the teeth resulting in tooth decay. The plaque also may attack the soft gum tissue of the mouth leading to gingivitis, which affects the gums, or periodontitis, which may affect all of the soft tissue and bone supporting the teeth. Gum recession, tooth sensitivity, yellowing and eroding teeth and are some of the common effects of poor oral hygiene.

Gingivitis is an inflammation of the gums characterized by redness, swelling, bleeding, and sensitivity. These changes result from an accumulation of biofilm along the gingival margins and the immune system's inflammatory response to the release of destructive bacterial byproducts. Investigations of the pathogenesis of periodontitis focus on the initiation and progression of the disease process, such as the progression from health to gingivitis, from acute to chronic inflammation, and from gingivitis to periodontitis. Gingivitis results in increased vascularity and morphological change in the vascular architecture, hemodynamics and tissue oxygenation. Monitoring and assessment of local inflammatory hemodynamic profiles such as tissue oxygen saturation (StO2), total tissue hemoglobin (tHb), deoxyhemoglobin (Hb) and oxygenated hemoglobin (HbO2) of gingiva during disease progression and response to therapy is crucial for understanding the pathophysiology. The early stages of gingivitis are reversible with effective treatment from oral cleaner, thorough brushing and flossing. Without adequate oral hygiene, however, chronic infections and periodontitis can develop.

Products are known that treat and reverse gingivitis and other oral conditions. Such products are effective at tooth whitening, stain removal, improving enamel health and erosion, improving gum health, treating dentin sensitivity, preventing caries, oral wound cleansing, bacteria removal, and treating oral bleeding and dry mouth. However, without proper diagnosis, it is difficult for consumers to know which products they can benefit from or receive a customized product to treat their specific oral health needs. What is therefore desired is a consumer-based diagnostic and treatment system which can diagnose oral conditions along with a consumer-based personalized oral cleaner dispenser that creates personalized oral cleaner to treat the diagnosed oral conditions. It would further be desired for the system to be integrated with a tele-dentistry platform for dentist recommended product formulations and dental routines.

BRIEF SUMMARY

The present disclosure may be directed to a method, device, and/or system for diagnosing and treating a condition of an oral cavity. In one aspect, a system includes a diagnostic device, a processor, and a product dispenser. The diagnostic device may include an illumination source configured to illuminate a portion of the oral cavity and a sensor configured to detect information relating to at least one of emission fluorescence or back scattered light relating to the illuminated portion of the oral cavity. The processor may be configured to receive the information relating to the at least one of emission fluorescence or back scattered light; determine the oral condition of the oral cavity based on the received information relating to the at least one of emission fluorescence or back scattered light; determine a combination of a plurality of ingredients that are expected to remedy the oral condition of the oral cavity; and cause identities of the plurality of ingredients to be transmitted. The product dispenser may house the plurality of ingredients and/or may include a mixing chamber. The product dispenser may include an interface configured to receive the identities of the plurality of ingredients expected to remedy the oral condition of the oral cavity; an agitator configured to mix the identified plurality of ingredients within the mixing chamber, thereby producing a product expected to remedy the oral condition of the oral cavity; and dispense the product expected to remedy the oral condition of the oral cavity via a nozzle of the product dispenser.

In another aspect, a method for diagnosing and treating a condition of an oral cavity may be provided. The method includes illuminating a portion of the oral cavity via a diagnostic device and detecting information relating to at least one of emission fluorescence or back scattered light relating to the illuminated portion of the oral cavity; receiving the information relating to the at least one of emission fluorescence or back scattered light; determining, via a processor, the oral condition of the oral cavity based on the received information relating to the at least one of emission fluorescence or back scattered light; determining identities of a plurality of ingredients that are expected to remedy the oral condition of the oral cavity; mixing, via a product dispenser, the identified plurality of ingredients thereby producing a product expected to remedy the oral condition of the oral cavity; and dispensing the product expected to remedy the oral condition of the oral cavity via a nozzle of a product dispenser.

BRIEF DESCRIPTION OF THE DRAWINGS

The present disclosure will become more fully understood from the detailed description and the accompanying drawings, wherein:

FIGS. 5A-5G show other example device(s) for dispensing an oral cleaner, as described herein.

DETAILED DESCRIPTION

Figure 1:
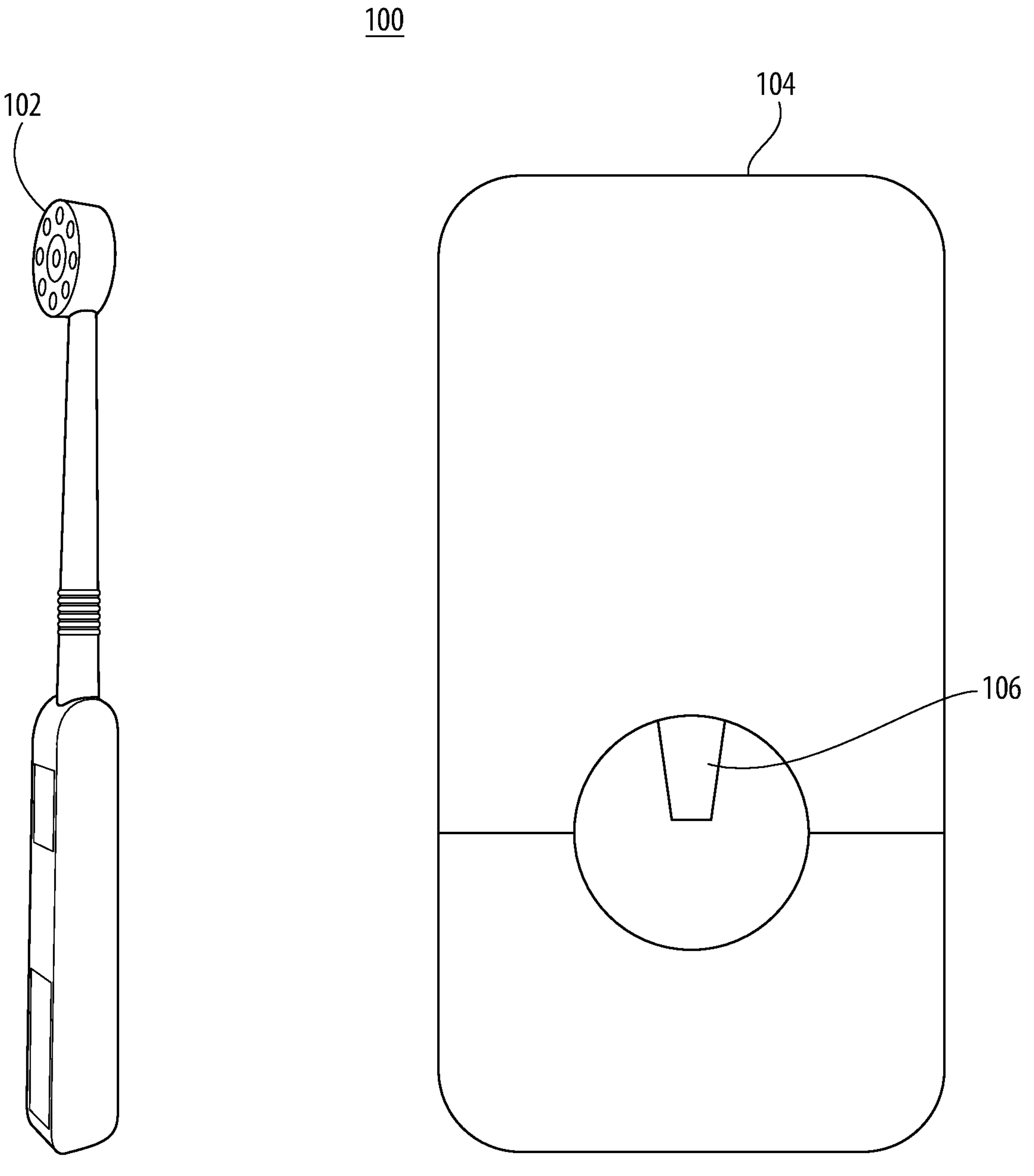
FIG. 1 shows an example system for diagnosing and treating an oral cavity condition, as described herein.

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present inventions. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require a particular orientation unless explicitly indicated as such. Terms such as "attached," "affixed," "connected," "coupled," "interconnected," "secured" and other similar terms refer to a relationship wherein structures are secured or attached to one another either directly or indirectly through intervening structures, as well as both movable or rigid attachments or relationships, unless expressly described otherwise. The discussion herein describes and illustrates some possible non-limiting combinations of features that may exist alone or in other combinations of features. Furthermore, as used herein, the term "or" is to be interpreted as a logical operator that results in true whenever one or more of its operands are true. Furthermore, as used herein, the phrase "based on" is to be interpreted as meaning "based at least in part on," and therefore is not limited to an interpretation of "based entirely on."

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Features of the present inventions may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device", or "device", and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present inventions may be embodied in the form of computer-implemented processes and apparatuses such as processor-based data processing and communication systems or computer systems for practicing those processes. The present inventions may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

Oral health problems can take many forms, such as tooth decay, tooth stain, tooth sensitivity, dry mouth, periodontal disease, and bad breath. A system, device, and method to provide home-care diagnostic is described herein. The diagnostic device may be used with a personalized oral cleaner dispenser that dispenses products based on diagnostics of the oral cavity of the user.

Periodontal disease and tooth caries may be caused by bacterial species in the mouth that interact with proteins present in saliva to form a film, known as plaque, that coats the teeth. If this biofilm build up progresses, the acid produced by the bacteria may attack the teeth, resulting in tooth decay. The plaque may attack the soft gum tissue of the mouth leading to gingivitis, which may affect the gums, or periodontitis, which may affect the soft tissue and bone supporting the teeth. Gum recession, tooth sensitivity, yellowing and eroding teeth, and the like are some of the common effects of poor oral hygiene.

Gingivitis is an inflammation of the gums characterized by redness, swelling, bleeding, and sensitivity. These changes result from an accumulation of biofilm along the gingival margins and the immune system's inflammatory response to the release of destructive bacterial byproducts. Investigations of the pathogenesis of periodontitis focus on the initiation and progression of the disease process, such as the progression from health to gingivitis, from acute to chronic inflammation, and from gingivitis to periodontitis. Gingivitis results in increased vascularity and morphological change in the vascular architecture, hemodynamics and tissue oxygenation. Monitoring and assessment of local inflammatory hemodynamic profiles such as tissue oxygen saturation (StO2), total tissue hemoglobin (tHb), deoxyhemoglobin (Hb) and oxygenated hemoglobin (HbO2) of gingiva during disease progression and response to therapy is crucial for understanding the pathophysiology. The early stages of gingivitis are reversible with effective treatment from oral cleaner, thorough brushing and flossing. Without adequate oral hygiene chronic infections and periodontitis can develop.

A home-based (e.g., consumer) diagnostic/treatment system which can diagnose oral conditions (such as plaque, caries, blood, bacteria, photoporphyrins, enamel health, tissue oxygenation, whiteness, and other useful parameters) in the oral cavity is described herein. The diagnostic/treatment system can improve user oral hygiene and reverse conditions such as gingivitis. In addition to a diagnostic device, a personalized (e.g., consumer) oral cleaner dispenser that creates and/or dispenses personalized oral cleaner to treat the diagnosed oral conditions and user reported conditions, such as dry mouth and sensitivity, may further enhance overall oral and physical health. The oral cleaner dispenser may create and/or dispense the oral cleaner based on one or more diagnostics provided by the diagnostic/treatment system. Although the examples herein relate to oral care diagnostics and treatments, it should be understood that such examples are for illustration purposes only and are not intended to be limiting. The diagnostic/treatment system may be used for diagnosing and/or treating one or more other conditions that relate to the personal care of a user, such as skin conditions, hair conditions, nail conditions, etc.

The diagnostic/treatment system may use light (e.g., photoluminescence) to determine diagnostics of an oral cavity of a user. For example, spectral properties of biomolecules in the oral cavity may be known. Two spectral detection modalities for diagnosing oral health may include fluorescence spectroscopy and absorption spectroscopy. Fluorescence spectroscopy may excel at detecting green fluorescence from tooth enamel and caries, and red fluorescence may be useful for detecting plaque, bacteria, and photoporphyrins. Using the fluorescence information, important parameters about tooth health may be determined. Absorption spectra may give information about chromophores in tissue. An example of static chromophores may include different types of melanin in the tissue and stains on teeth. Examples of non-static chromophores may include oxygenated and deoxygenated blood. Absorption spectroscopy may be useful in detecting tissue parameters, such as blood concentration, blood oxygenation, and/or tooth whiteness. Other biomolecules may be detected using absorption/reflection spectroscopy.

A system, apparatus, and/or method for diagnosing oral hygiene and dispensing personalized oral care and dental hygiene products based on the diagnostics is provided herein. An oral hygiene device may be used in the oral cavity for hygiene monitoring and health diagnostics. The oral hygiene device may be inserted in or moved about the oral cavity. Diagnostics relating to the oral cavity may be acquired and/or determined by detecting fluorescence emission and/or optical reflection/absorption of incident light. A multichannel spectrometer or spectrophotometer may be used for detecting the light. The optical properties of biomolecules may be used to detect plaque, caries, blood, bacteria, photoporphyrins, enamel health, tissue oxygenation, whiteness, and other useful parameters in the oral cavity.

The hygiene device may use an onboard camera and/or inertial measurement sensor (IMU) to determine the location of the optical radiation in the oral cavity. In examples artificial intelligence (e.g., deep learning) techniques may be used to determine the location of the optical radiation in the oral cavity. The oral hygiene device may have one or more onboard microcontroller units (MCUs) and/or microprocessor units (MPUs). The one or more MCUs and/or MPUs may have onboard memory and/or a wireless module. The one or more MCUs, MPUs, IMUs, multichannel spectrometers, onboard memories, and/or wireless modules may be an integrated system fabricated on a single or multiple connected chips (such as a system on a chip (SoC)). The SoC may diagnose the received optical radiation and/or assign the diagnosis to the determine location in the oral cavity. The SoC may perform this diagnosis before, during, or after determining the location of the oral cavity. The information may be transmitted (e.g., streamed) to a personalized care oral cleaner dispenser, as described herein. The oral cleaner dispenser may use the received information to create a personalized oral cleaner for the user. As a result, the personal care of the user may be enhanced as the oral cleaner is tailored to treat the diagnosed conditions of a user of the system.

The oral diagnostic device may be wirelessly connected to an oral care and dental hygiene product dispenser (e.g., oral cleaner, oral dispenser, etc.). The oral care and dental hygiene product dispenser may customize the production, mix, dispensing, and the like of the oral care and cleaning product based on the oral health and hygiene of the user (e.g., the diagnostics relating to the oral health and hygiene of the user). As a result, the oral hygiene of a user may be diagnosed and/or a personalized oral care and cleaner may be dispensed to improve the oral hygiene and/or personal health of a user.

Referring now to the figures, FIG. 1 shows an example system 100 including a hand-held oral hygiene device 102 that is used to perform diagnostics of the oral cavity. The hygiene device 102 may be coupled to an oral care and dental hygiene product dispenser 104 (oral cleaner dispenser 104) in examples, although in other examples the hygiene device 102 may be separate from an oral care and dental hygiene product dispenser 104. The hygiene device 102 may transmit (e.g., wirelessly transmit) diagnostic information to the oral care and dental hygiene product dispenser 104. The oral cleaner dispenser 104 may use the diagnostic information to formulate and dispense (e.g., dispense via nozzle 106) a personalized oral product (e.g., a cleaning product, whitening product, remediation product, etc.) for treating the diagnosed conditions. The oral cleaner may be formulated and/or dispensed in at least one of a gel, paste, or liquid form.

Figures 2A, 2B, 2C, 2D:
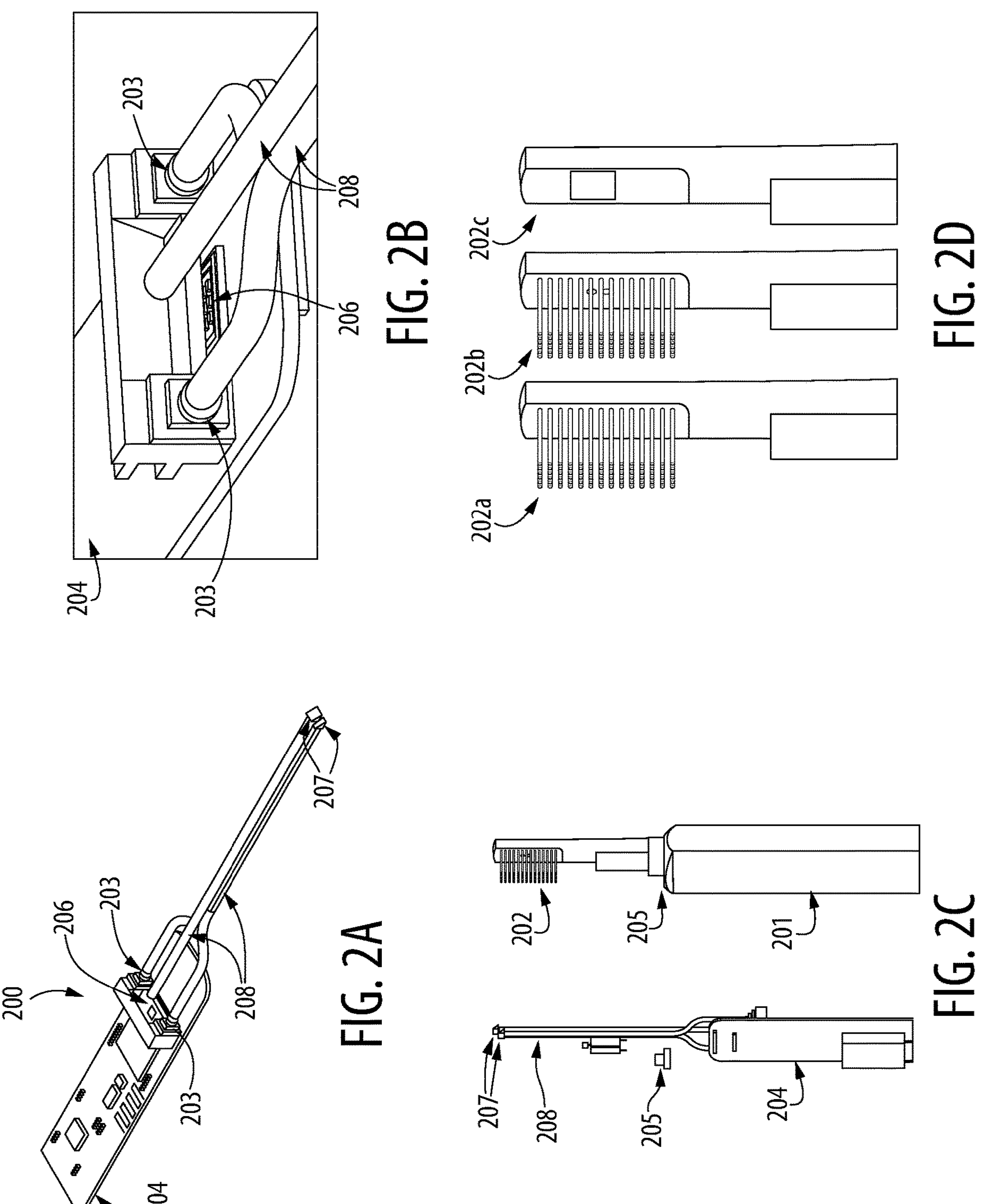
FIGS. 2A-2D show an example device for diagnosing an oral cavity condition, as described herein.

An example hygiene device 200 is shown in the different views of FIGS. 2A-2D. FIG. 2A shows SoC 204 and light-guides 208. FIG. 2B shows a zoomed region of SoC 204. FIG. 2C shows hygiene device 200 skeleton and body 201. FIG. 2D shows alternate hygiene device heads that may be used by device 200. As shown on FIG. 2C, the hand-held hygiene device 200 has a body 201 for holding and a head 202 for inserting into and around the oral cavity. The head 202 may have different attachments, such as attachments 202*a*, 202*b*, 202*c* (shown on FIG. 2D). The attachments, for example, may include mirrors for detecting light in difficult to reach locations of the oral cavity.

Illumination sources (e.g., LEDs) may be provided in the hygiene device 200. For example, LEDs 203 may be embedded in, on, and/or around the head 202 or SoC 204 for optical excitation and absorption/scattering illumination. The LEDS (e.g., excitation LEDs) may be ultra-violet (UV), purple, blue, green, red, NIR, or Mid-IR LEDs. The LEDs may be in the body 201 of the hygiene device 200 and/or light (e.g., illuminated from the LEDs) may be carried to the illumination area via optical fibers, light pipes, and/or through free space. Laser diodes (LDs) (e.g., a combination of LEDs and LDs) may be used for illuminating the sampled area.

The hygiene device 200 may include a camera 205 embedded in the body 201. The camera 205 may face the user. One or more cameras 205 may be mounted on the head 202 and/or body 201 of device 200. The camera 205 may be a type of CCD, CMOS, or other array based UV/VIS/NIR/SWIR/FWIR/IR or thermal sensor. The camera 205 may be a monochrome, bi-chrome, RGB, multispectral, hyperspectral, and/or thermal imaging camera. One or more spectral sensors 206 may be used to detect the emission fluorescence and/or back scattered light. The back scattered light may be polarized or unpolarized. One or more spectral sensors 206 may be mounted inside the body 201 on the SoC 204 of the hygiene device 200.

The light may be collected through the head 202 using one or more collection lenses and/or reflection mirrors 207 into one or more light-guides 208. The light-guide may be a fiber optic, light pipe, liquid light-guide, crystal light-guide, or other free space device. The light-guide end may terminate above the one or more spectral sensors 206. The output light may be directly incident on the spectral sensors or reshaped using an optical lens or curved mirror. In an example of multiple spectral sensors, the colors of the collected light may be separated using a dichroic mirror or dichroic beam splitter and/or directed into the respective spectral sensors either directly or using a lens or curved mirror. The camera 205 and one or more spectral sensors 206 may be connected to a SoC 204. The SoC 204 may be equipped with a wireless module for streaming data to the personalized care oral cleaner dispenser 104. The SoC may have an onboard memory chip for short-term or long-term information and instruction storage. In some embodiments, the hygiene device SoC is integrated with an IMU for motion detection.

Figure 3:
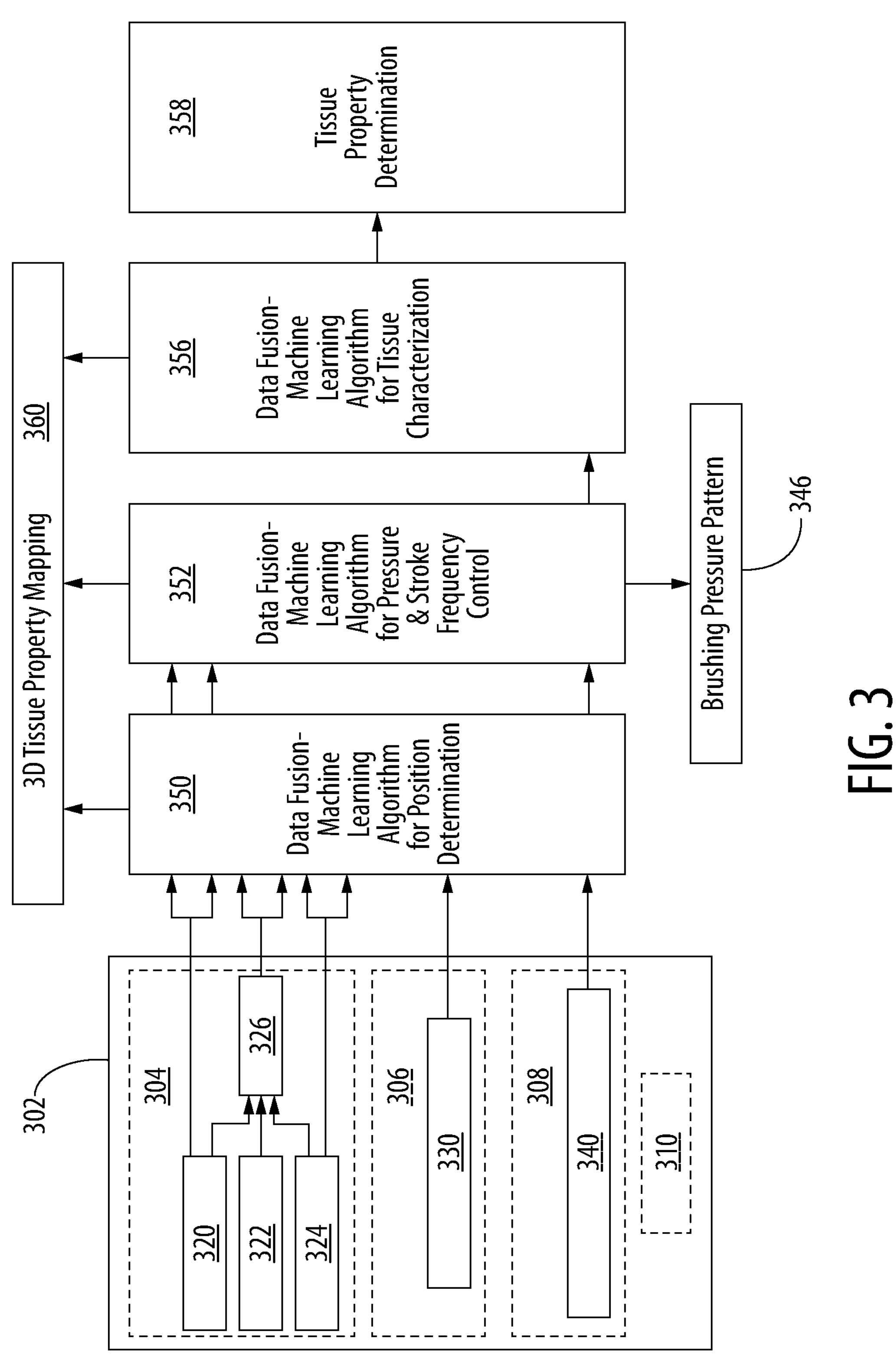
FIG. 3 shows an example process diagram for diagnosing an oral cavity condition, as described herein.

FIG. 3 shows a block diagram of the hygiene device 302, as described herein. Hygiene device 302 may include one or more components, such as one or more IMU sensors 304, cameras 306, sensors 308 (e.g., spectral sensor), and/or illumination sources 310. IMU sensors 304 may include one or more components, such as an accelerometer 320, magnetometer 322, gyroscope 324, and the like. The components of the IMU sensors 304 may perform one or more actions, such as a calibration 326. Camera 306 may include one or more components, such as a camera/position sensor 330. Sensor (e.g., spectral sensor) 308 may include one or more components, such as a spectrometer/position sensor 340.

The one or more components of hygiene device 302 may perform one or more operations, such as a position determination 350. The position determination 350 may be performed via a data fusion machine learning technique. The one or more components of hygiene device 302 may perform a pressure and/or stroke frequency control 352. The pressure and/or stroke frequency control 352 may be performed via a data fusion machine learning technique. The pressure and/or stroke frequency control 352 may result in a determination of a brushing pressure pattern 346. The one or more components of hygiene device 302 may perform a tissue characterization 356. The tissue characterization 356 may be performed via a data fusion machine learning technique. A determination of tissue property 358 may result, as described herein.

Illumination sources 310 may be alternated between excitation illumination and scattering illumination. During excitation illumination, the spectral sensors 308 may be used to collect the induced fluorescence. The fluorescence signal may be used to detect the green fluorescence from enamel and the red fluorescence from plaque biofilms, carries, bacteria and photoporphyrins. The biofilms may be found on hard and/or soft tissues. The backscattered light (e.g., from the broadband illumination) may be used to detect blood, tissue oxygenation, and/or tooth whiteness, as described herein. In examples the absorption may be used to diagnose blood oxygenation, blood concentration, vasculature density, lesions, and/or oral cancers.

The hygiene device may acquire optical data, as described herein. The hygiene device may determine the location of the hygiene device based on the acquired optical data. For example, the hygiene device may determine its location in or around the oral cavity using either the camera (e.g., optical data provided by the camera), an inertial measurement unit (IMU), or a combination of the camera and IMU. The IMU may include an accelerometer, magnetometer, gyroscope, etc. Artificial intelligence (e.g., a deep learning neural network) may train the device on the oral cavity data (e.g., location data) relating to one or more users. During a training session, the user may be instructed to move the device to one or more areas in or around the oral cavity, such as for a predetermined amount of time. The captured images and/or IMU data may be used to train the neural network to understand the location in or around the oral cavity, as shown in FIG. 3.

An IMU sensor may be used to improve position accuracy. In examples in which an IMU sensor is used to improve position accuracy, the IMU data may be analyzed (e.g., first analyzed) by the SoC, and the orientation of the hygiene device may be determined. The orientation may be used to superimpose a frequency onto the camera image acquired at the IMU orientation. Superimposed images may be frequency grating patterns that include frequency changes with the specific device orientation. Such techniques may minimize computational resources of the SoC. The position data determined by the neural network may be time stamped and/or combined with spectral analysis (e.g., spectral analysis taken at or near the same time). In other examples, techniques (e.g., artificial intelligence techniques) and/or data may be used to control pressure and/or stroke frequency, characterize tissue, and/or determine tissue properties.

Tissue properties (e.g., 3D tissue properties) may be mapped. For example, a 3D tissue property mapping 360 may be performed. Data may be used to make a hygiene map of the oral cavity. The data and/or map may be used to determine and/or provide a brushing pressure pattern. The diagnosis information may be transmitted to an external device (such as a cloud server), using the onboard wireless module, and a chart (e.g., an online chart) may determine an oral cleaning formula ideal for the specific oral health map of the user. In examples, the chart may be stored in the SoC memory and/or the data may be directly transmitted (e.g., streamed) to the personalized care oral cleaner dispenser. The chart may be stored in the SoC of the personalized care oral cleaner dispenser.

Figures 4A, 4B:
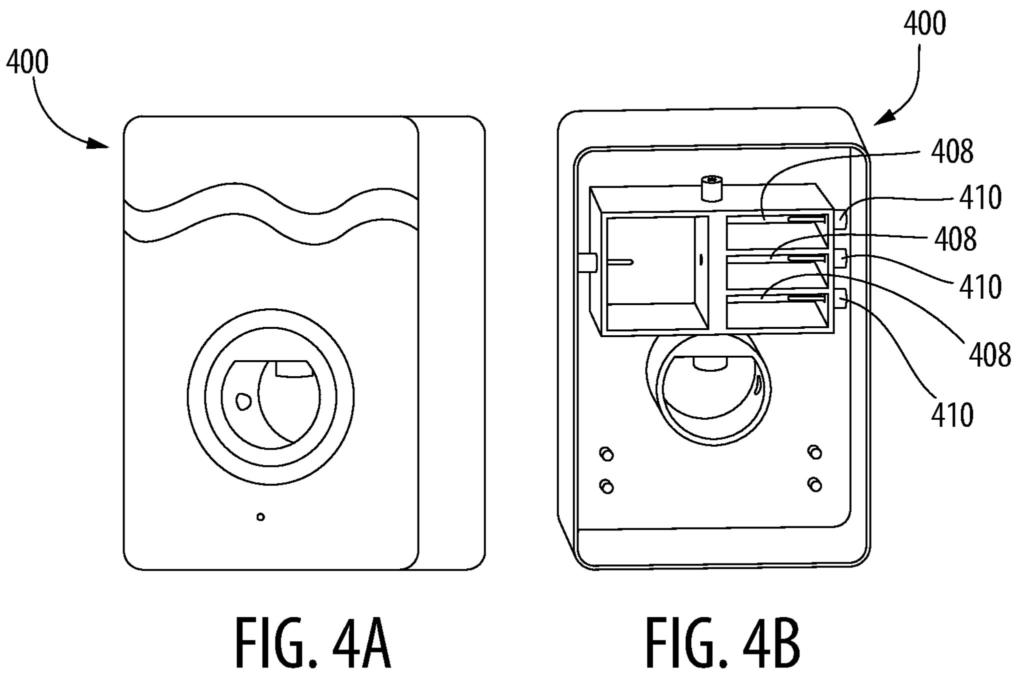
FIGS. 4A-4C show an example device for dispensing an oral cleaner, as described herein.
Figure 4C:
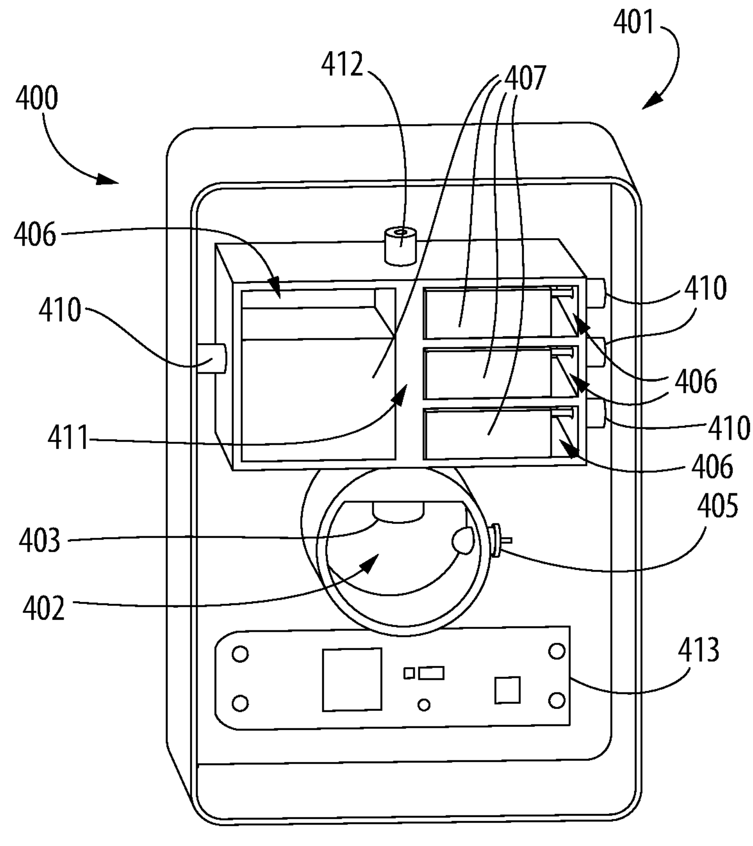

FIGS. 4A-4C show schematics of an example oral cleaner dispenser 400 (similar to device 200 described herein). FIG. 4A shows a front view of oral cleaner dispenser 400. FIG. 4B shows a back view of oral cleaner dispenser 400 with back panel and components removed. FIG. 4B is a view similar to FIG. 4B, with components inserted.

As shown on FIG. 4C, dispenser device 400 has a body 401 and a cavity 402 for inserting the head of a hygiene device. The cavity 402 may include a dispensing nozzle 403. The nozzle 403 may have one or more output holes. One or more ingredients (e.g., customized ingredients) may be combined and/or output. For example, nozzle 403 may combine ingredients and/or output a customized oral cleaner. The oral cleaner (e.g., the final oral cleaner) may be one or more of a paste, gel, liquid, or the like.

The cavity 402 may contain a sensor 405 to detect when a hygiene head or container for ingredient collection has been inserted. The sensor 405 may dispense (e.g., cause the dispenser to dispense) the one or more personalized oral cleaner(s). In examples, a push lever may be used with a sensor or instead of a sensor. The body 401 may have one or more slots 406, for example, to insert ingredient cartridges 407 for making the personalized oral cleaner. A system (such as a slide and lock system) may hold (e.g., firmly hold) the ingredient cartridges 407 in place. A lever (e.g., quick release lever) may remove the used cartridges 407. A window or optical encoder may be included in the device to determine when cartridges need replacement.

The output end of one or more (e.g., each) ingredient cartridge 407 may be sealed with a film. The film may be ruptured when inserted into the body 401. Rupturing of the film may expose ingredients, such as sanitary ingredients. The ingredient cartridge 407 may have a portion (e.g., pressure plate 408) that may cause (e.g., may cause when pushed) a positive pressure on the inside of the cartridge 407. A positive pressure on the inside of the cartridge may cause the ingredients to normalize the pressure, for example, by exiting the output end.

Solenoid motors 410 may be provided inside the body. The solenoid motors 410 may touch the surface of the inserted ingredient cartridges 407. When activated, the solenoid motors 410 may apply a force to the pressure plates 408, causing the ingredients to flow from the cartridge 407 and into the mixing chamber 411 located between the center of the cartridge rack. One or more motors 412 may force the ingredients through the mixing chamber. In examples, the solenoid motors may be replaced with rotational motors attached to a rotational-to-linear converter, piezo-motors, stepper motors, or other forms of motors for forcing ingredients through the chamber. For example, the motors may be replaced with a pneumatic pump or other type of pump cable of moving the ingredients out of the ingredient cartridge and through the nozzle. The motors may be controlled using one or more SoCs 413. The one or more SoCs 413 may be connected to a wireless module for receiving wireless information. In examples, the one or more SoCs 413 may transmit (e.g., stream) data for mechanical diagnostics and/or for communicating with a smart device (such as a smart phone and the like). The one or more SoCs 413 may include an onboard memory chip for short-term or long-term information and/or instruction storage.

Figure 5D:
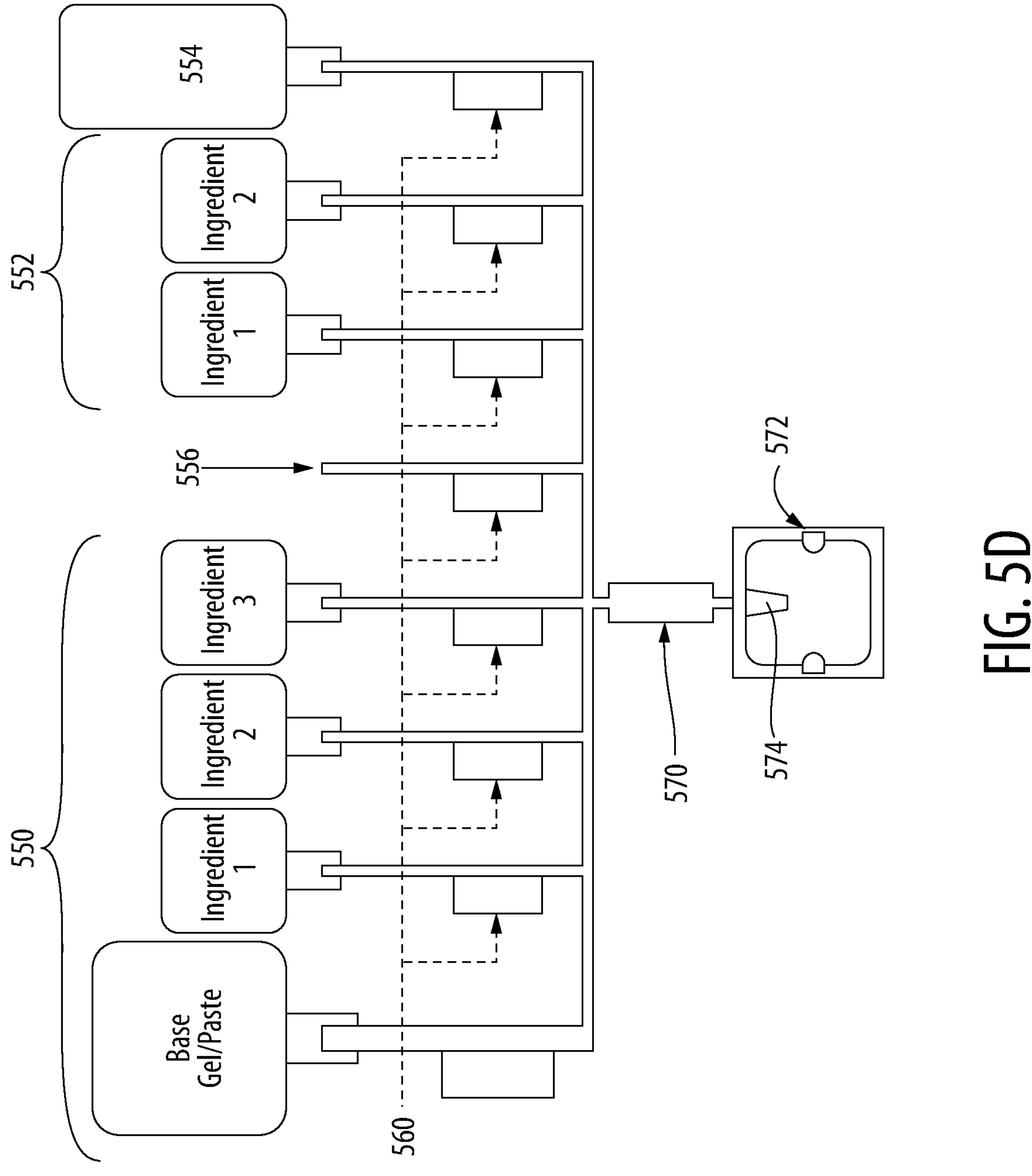

FIGS. 5A-5G show schematics of another example of a personalized care oral cleaner dispenser 500. FIG. 5B shows an inside view of the cartridge-pump system of the oral cleaner dispenser 500. FIG. 5C is similar to FIG. 5B, but with a side view and components labeled. The dispenser device 500 may have a body 501 and/or a cavity 502 for inserting the head of a cleaning device and/or a fluid container. The cavity 502 may include a dispensing nozzle 503. The nozzle 503 may have one or more output holes that may lead to a mixing chamber 504 that may combine ingredients and/or output a customized oral cleaner. The cleaner may be in at least one form of a paste, gel, liquid, and the like, as the final product(s).

The mixing chamber 504 may have an active agitator 505 for mixing the ingredients. The mixing chamber 504 may be a helix shaped chamber with, for example, internal fins which mixes (e.g., passively mixes) ingredients using the pressure and resulting vortex. The agitator 505 may be a piezoelectric or other type of small mixing device. The cavity 502 may contain a sensor. The sensor may detect when a hygiene device head or container for ingredient collection has been inserted. After detection, the dispenser may dispense the one or more personalized oral cleaner(s). In examples, a push lever may be used instead of, or along with, a sensor. The body may have one or more slots to insert ingredient cartridges for making the personalized oral cleaner. The cartridges may be organized by type. For example, the cartridges may contain gel, paste 507*a*, and/or liquid 507*b*.

Cartridges may be replaced with customizable cartridges 507*c* and/or base ingredient cartridges 507*d*. Motors (e.g., miniature piezoelectric motors 510) may force ingredients through the chamber and/or close the cartridge from back flow of other ingredients by adjusting pump pressure. The liquid and/or paste/gel flow chambers may include shutoff valves 511 to prevent back flow from the different (e.g., two different) matter forms into the respective irrigation chambers. To clean the flow chambers, cleaning fluid cartridges 507*e* may be used to flush and clean ingredients from the chamber after use.

The motors may be controlled using one or more SoCs inside the body. The one or more SoCs may be connected to a wireless module for receiving wireless information. In some examples, the one or more SoCs may transmit (e.g., stream) data for mechanical diagnostics and/or for communicating with a device (e.g., a smart device, such as a smart phone and the like). The one or more SoCs may include an onboard memory chip for short-term or long-term information and/or instruction storage.

FIG. 5D shows an alternative drawing of dispenser 500 that is capable of mixing and/or dispensing ingredients, such as pastes, gels, and liquids. For example, toothpaste/gel 550, mouthwash 552, and/or a self-cleaning solution 554 may be provided. One or more other ingredients may be provided, for example, via an ingredient port 556. The ingredients may be provided via a pump, such as a miniature PZT pump/mixers 560, 570. An optical sensor 572 may identify the ingredients prior to the ingredients being dispensed via dispenser 574.

Figure 5E:
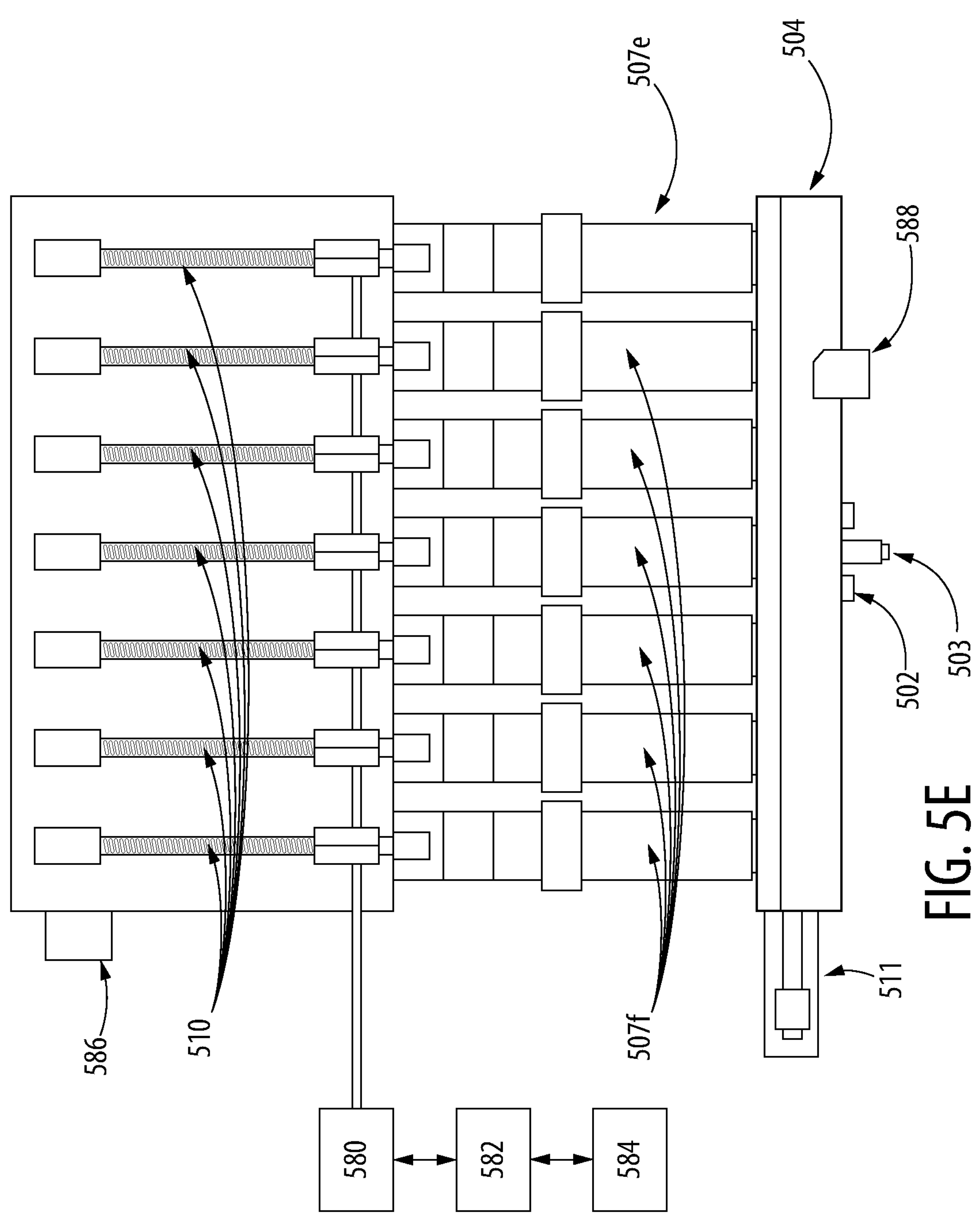

FIG. 5E shows an alternative drawing of dispenser 500 including a squiggle motor driver 580, control logic driver 582, and diagnostic data from one or more sources, such as an oral scanner. The example setup may use load motors 510 for insertion and/or removal (e.g., easy insertion and/or removal) of cartridges. FIG. 5E further shows liquid glide technology 507*f*, 507*e*, cavity 502, dispenser nozzle 503, actuator 511, loading actuator 586, and mixing chamber 504 of example dispenser 500. Actuator 511 may be a self-cleaning valve actuator. A proximity sensor 588 may be located near dispenser nozzle 503.

Figure 5F:
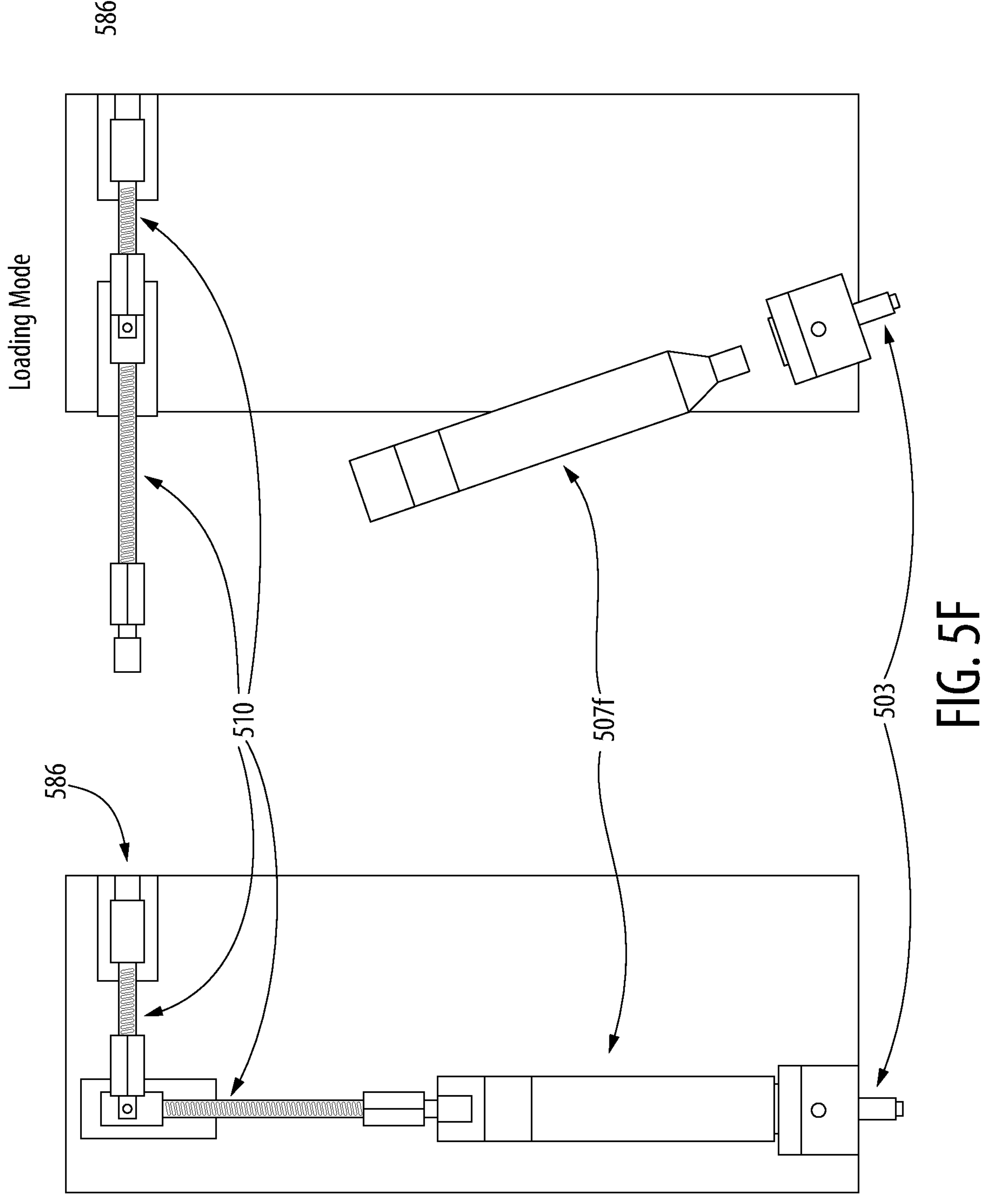
Figure 5G:
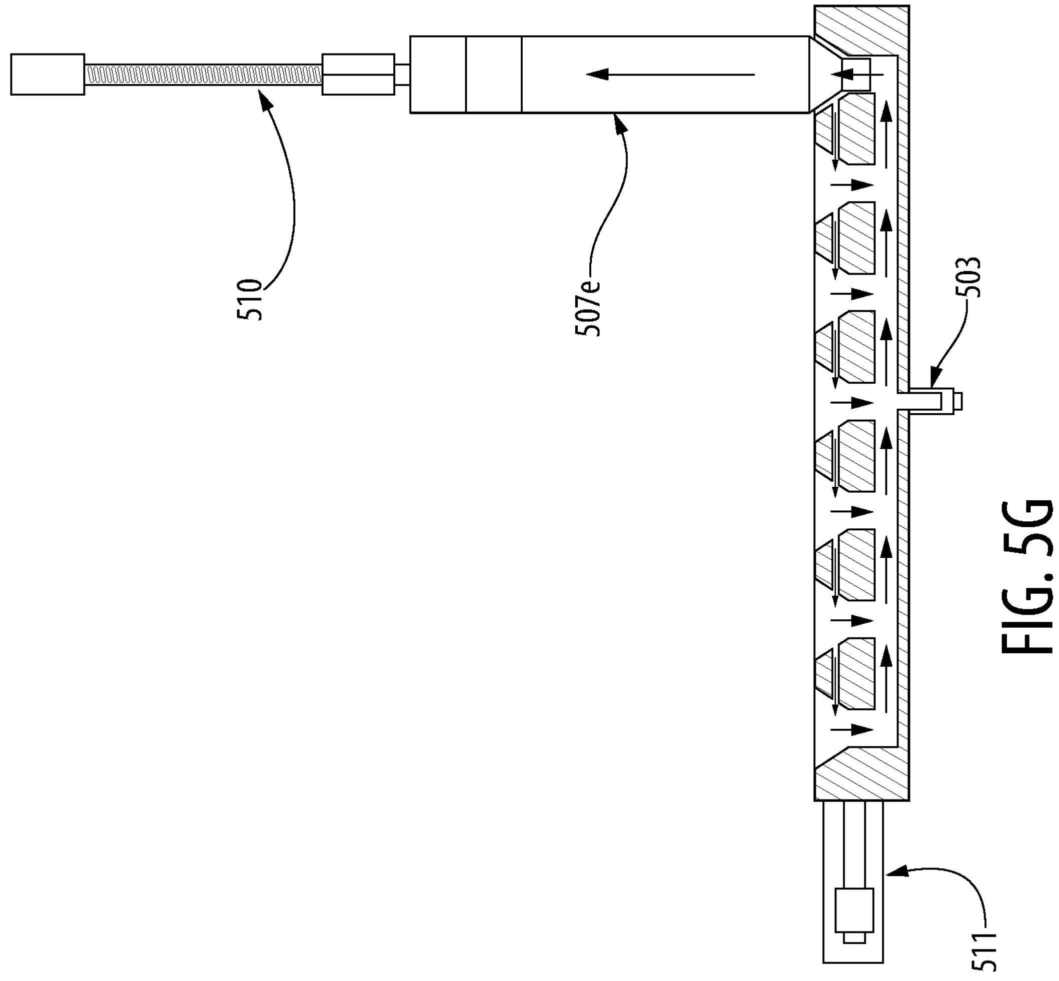

FIG. 5F shows an alternative drawing of loading and unloading paper cartridge, as shown on FIG. 5E. FIG. 5F shows loading actuator 586, load motors 510, liquid glide technology 507*f*, 507*e*, and dispenser nozzle 503. As shown on FIG. 5F, the load motors 510 may be multiplexed as ingredient dispenser motors, which may be capable of forcing ingredients through the chamber. FIG. 5G shows an example in which the dispenser 500 may include a self-cleaning mode and/or may contain a self-cleaning chamber. Self-cleaning valve actuator 511 may close ingredient cartridges, for example, when self-cleaning mode is activated. A cartridge (e.g., a separate cartridge) with cleaning liquid may remain open and/or an actuator may force cleaning liquid through the mixing chamber. The cartridges may be biodegradable (such as paper cartridges) that may include liquid glide technology 507*f*.

Figure 6:
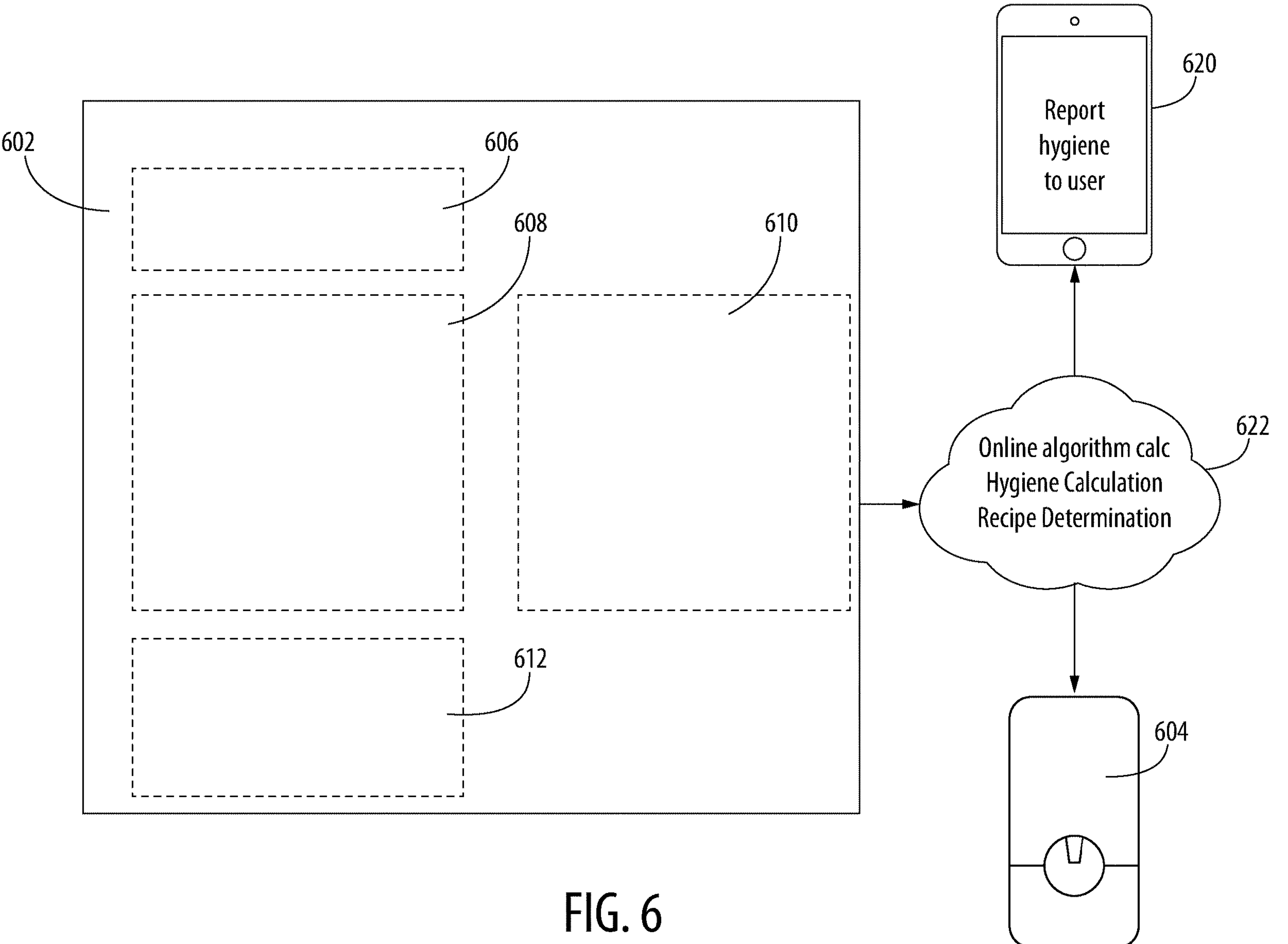
FIG. 6 shows an example process diagram for dispensing an oral cleaner, as described herein.

FIG. 6 shows a block diagram of an example method for using a personalized care oral cleaner dispenser, as described herein. The hygiene device 602 may wirelessly send oral hygiene diagnostics to the personalized care oral cleaner dispenser 604. The hygiene device 602 may include a location component 606. The location component 606 may include a camera and/or an IMU that performs location detection (e.g., location detection of the hygiene device 602). The hygiene device 602 may include a spectral sensor 608. The spectral sensor 608 may perform (e.g., determine) plaque detection, bacteria detection, enamel health detection, color (e.g., whiteness) value(s), blood concentration(s), tissue oxygenation(s), etc. The hygiene device 602 may include a mapping component 610. The mapping component 610 may perform a mapping. For example, the mapping component 610 may include a mapping of plaque, bacteria, enamel health, whiteness/staining, blood concentration, tissue oxygenation, etc.

The hygiene device 602 and/or oral cleaner dispenser 604 may include one or more wireless modules, such as wireless module 612. The oral cleaner dispenser 604 (e.g., wireless module 612 of the oral cleaner dispenser 604) may receive data (e.g., may receive data from the hygiene device 602, a mobile device, an external server, etc.), such as data relating to ingredients for a toothpaste or other oral cavity product that may be recommended by a dentist through an integrated tele-dentistry platform. The oral cleaner dispenser 604 (e.g., wireless module 612 of the oral cleaner dispenser 604) may access a catalog stored in the oral cleaner dispenser memory or an online catalog. For example, the hygiene device 602 may transmit (e.g., directly transmit) the data from the catalog. The hygiene device 602 may transmit (e.g., wirelessly transmit) data to an external device (e.g., the cloud). The oral cleaner dispense device may access the data from the external device (e.g., cloud). The catalog may be a look-up table that contains ingredient mixture recipes for a range of detected oral conditions.

The SoC may prepare the solenoid motor(s) to dispense an amount (e.g., a predefined amount, a desired amount, a correct amount) of each ingredient, for example, after the diagnostics are matched with the most appropriate treatment ingredients to treat the diagnosed conditions. The ingredient may be dispensed in a paste form, a liquid form, a gas form, and the like. The ingredient may be dispensed through the output nozzle of the oral cleaner dispenser. The oral cleaner dispenser may wait for a user to insert a hygiene device head. When a hygiene device head or fluid container is inserted under the nozzle, the SoC may control the motors to dispense the ingredients from the ingredient cartridges to match to recipe in the catalog.

Data (e.g., data scores) determined and/or acquired from the hygiene device may be stored in the hygiene device, a mobile device 620, an external device (e.g., the cloud), and the like. Data may be transmitted via a network 622, such as the Internet. The data may be used to track user hygiene, such as hygiene improvements or regression over time. Hygiene improvements or regression may relate to one or more of tooth whiteness, caries, plaque, enamel health, bacteria concentration, blood, tissue health, and the like. The hygiene improvements or regression may relate each of the areas of oral cavity and/or to an overall score of hygiene of the oral cavity.

Figure 7:
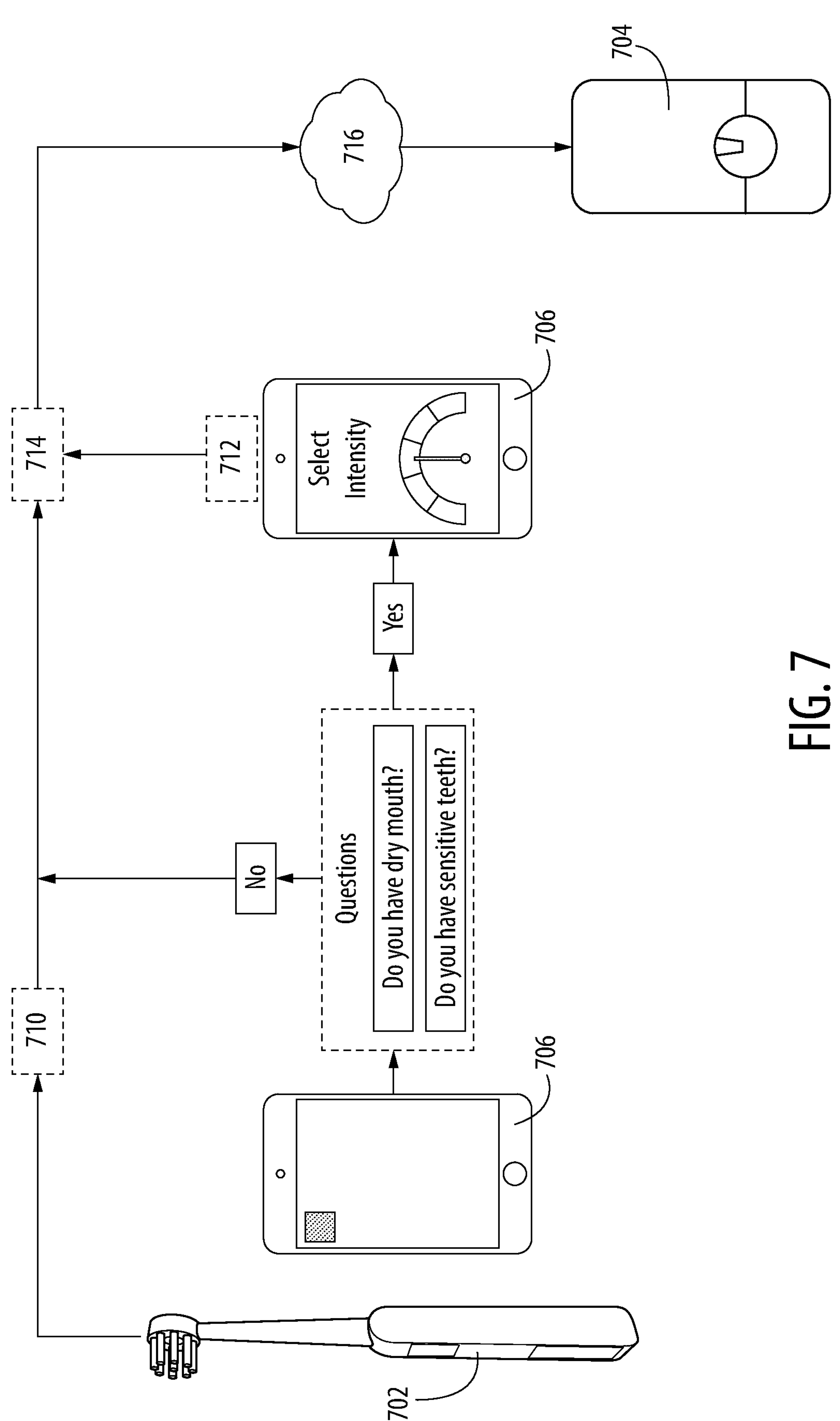
FIG. 7 shows an example process diagram for using an example device for diagnosing an oral cavity condition and inputting user information, as described herein.

FIG. 7 shows a block diagram for combining input from hygiene device 702 and user of hygiene device 702. Input (e.g., manual input) may be provided to the oral cleaner dispenser via buttons on the device and/or via a connected device (such as a mobile device 706, table, computer, etc.). The hygiene device 702 may perform a device diagnostic 710, a self (e.g., user) diagnostic 712, or a combination diagnostic 714.

Dispenser 702 may be connected to one or more devices (e.g., hygiene devices 702, mobile devices 706, etc.) via an application ("app") installed on the dispenser 702 or device, such as mobile device 706. Information not detected by the hygiene device 702 may be manually entered through a user interface or application of the mobile device 706. Such information may include conditions (e.g., difficult to diagnose conditions), such as dry mouth, dry mouth level, sensitivity, sensitivity level, sensitive area of specific tooth, as well as one or more other conditions. For example, as shown on FIG. 7, the application may ask questions, such as whether the user has dry mouth and/or if the user has sensitive teeth.

As shown on FIG. 7, the user may be asked, via the application of the mobile device 706, if she is (or was) experiencing conditions (e.g., common and/or difficult to diagnose conditions), such as sensitivity or dry mouth. If the user is experiencing one or more conditions, the application may ask more detailed questions about location and severity of pain/sensitivity and severity of the condition (e.g., dry mouth). To simplify the reporting, a severity scale (e.g., scale from 1 to 10) may be used and/or provided via mobile device 706. Such reporting and/or questions may be used so that a self-diagnostic 712 may be performed. The user may enter additional information, such as flavor preferences for the dispensed oral cleaner. The manually input information may be combined with the diagnosed information 710, at 714. A stored or online catalog may be referenced, and/or the oral cleaner 704 may dispense a product that is determined to be effective and/or referred by the user (e.g., more effective and/or more referred by the user).

The hygiene device 702 may send hygiene information to an external device (e.g., the cloud) via a network 716, such as the Internet. On the cloud, for example, there may be an updatable catalog that uses the hygiene score to determine the treatment and/or recipe desired to improve oral health. The recipe may be transmitted from the cloud to the oral cleaner dispenser 704. The oral cleaner dispenser 704 may create the received recipe. In examples, artificial intelligence (e.g., machine learning, deep learning, neural network, etc.) techniques may be used to adjust the recipe. When using artificial intelligence techniques, the online algorithm may be trained to identify (e.g., determine) statistically significant differences in hygiene score over predetermined periods of times (e.g., scores ranging from days to months). In examples, the machine learning techniques may be stored and/or implemented on the dispenser's SoC. In some examples, the product catalog may be stored on the SoC of the oral cleaner dispenser 704. If a certain treatment is showing to have negative effects on hygiene or bleeding, machine learning techniques may change the recommended dosage(s) and/or may seek statistically reduced symptoms. The machine learning technique may optimize (e.g., dynamically optimize) the dose(s) and/or ingredient mixtures for the most effective and/or desired treatment.

Figure 8:
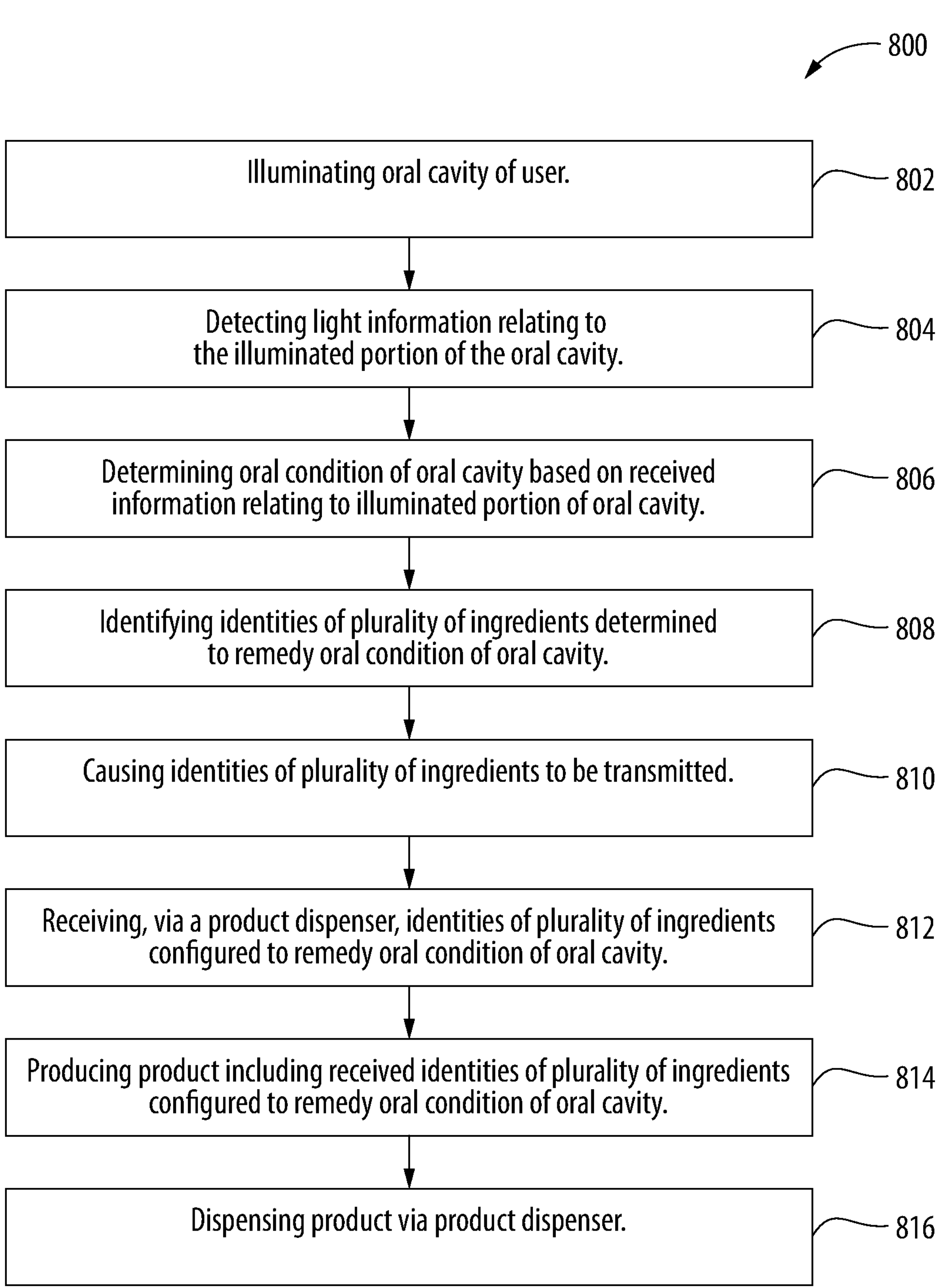
FIG. 8 shows an example process for diagnosing and treating an oral care condition using the system, method, and devices described herein.

FIG. 8 shows an example process 800 for diagnosing and treating an oral care condition using the system, method, and devices described herein. At 802, an oral cavity of a user may be illuminated, as described herein. The oral cavity of the user may be illuminated via an illumination source, such as an LED or the like. The illumination source may be coupled to and/or housed within a diagnostic device, such as hand-held oral hygiene device 102. At 804, light information may be detected. For example, emission fluorescence and/or back scattered light relating to the illuminated portion of the oral cavity may be detected. At 806, an oral condition of the oral cavity may be determined. For example, an oral condition of the oral cavity may be determined based on received information relating to the illuminated portion of the oral cavity.

Identities of one or more ingredients may be identified, at 808. The one or more ingredients may be determined by one or more of an oral hygiene device, a mobile device, a product dispenser, a server (e.g., a cloud server), and the like. The one or more ingredients may be determined to (e.g., expected to) remedy the oral condition of the oral cavity. For example, the one or more ingredients may be expected to remedy, address, treat, etc., the oral conditions of the oral cavity. Although the one or more ingredients may be expected to remedy, address, treat, etc., the oral conditions of the oral cavity, it should be understood that results are not guaranteed. As an example, the one or more ingredients are not guaranteed to remedy, address, treat, etc., the oral condition.

At 810, the identities of the one or more ingredients may be transmitted. For example, the identities of the one or more ingredients may be transmitted to a mobile device, a product dispenser, a server (e.g., a cloud server), and the like. The identities of the one or more ingredients may be transmitted wireless and/or via a wire. At 812, the product dispenser may receive the identities of the plurality of ingredients. The product dispenser may house the one or more ingredients. The product dispenser may include a mixing chamber for mixing the one or more ingredients, thereby producing a product (e.g., product determined to remedy the oral condition). At 814, the product dispenser may produce a product, for example, by mixing the identified plurality of ingredients. The plurality of ingredients may be mixed in the product dispenser, in examples, although in other examples the plurality of ingredients may be entirely mixed (or partially mixed) in one or more other devices. At 816, the product (e.g., the mixed product) may be dispensed. For example, the product may be dispensed in a gel, paste, liquid, or other form. The product may be dispensed on to oral hygiene device 102. The user may use the oral hygiene device 102 with the product to remedy a condition, such as to whiten a tooth, remedy gingivitis/plaque, or the like.

While the inventions have been described with respect to specific examples including presently preferred modes of carrying out the inventions, those skilled in the art will appreciate that there are numerous variations and permutations of the above described systems and techniques. It is to be understood that other embodiments may be utilized and structural and functional modifications may be made without departing from the scope of the present inventions. Thus, the spirit and scope of the inventions should be construed broadly as set forth in the appended claims.

What is claimed is:

1. A system for diagnosing and treating a condition of an oral cavity, comprising:

a diagnostic device comprising:

an illumination source configured to alternately illuminate a portion of the oral cavity with (i) excitation illumination configured to induce emission fluorescence from the portion of the oral cavity and (ii) scattering illumination configured to produce back scattered light from the portion of the oral cavity; and a sensor configured to detect information relating the emission fluorescence and the back scattered light, wherein the information comprises fluorescence information and absorption information, the absorption information being derived from the back scattered light, the fluorescence information being used to detect plaque and bacteria within the oral cavity, and the absorption information being used to determine chromophore information in one or more tissues of the oral cavity;

a processor configured to:

receive the information relating to the emission fluorescence and the back scattered light, including the fluorescence information and the absorption information;

determine the oral condition of the oral cavity based on the received information relating to the emission fluorescence and the back scattered light;

determine a plurality of ingredients that are expected to remedy the oral condition of the oral cavity; and cause identities of the plurality of ingredients to be transmitted; and a product dispenser housing the plurality of ingredients and comprising a mixing chamber, the product dispenser comprising:

an interface configured to receive the identities of the plurality of ingredients expected to remedy the oral condition of the oral cavity;

an agitator configured to mix the identified plurality of ingredients within the mixing chamber, thereby producing a product expected to remedy the oral condition of the oral cavity; and a nozzle configured to dispense the product expected to remedy the oral condition of the oral cavity.

2. The system of claim 1, further comprising a camera, the camera comprising at least one of a monochrome camera, bi-chrome camera, red-green-blue (RGB) camera, multi-spectral camera, hyperspectral camera, or thermal imaging camera.

3. The system of claim 2, wherein the diagnostic device is configured to determine the location of the diagnostic device within or about the oral cavity via optical data provided via the camera.

4. The system of claim 1, wherein the diagnostic device further comprises an inertial measurement unit (IMU) sensor configured to determine the location of the diagnostic device within or about the oral cavity.

5. The system of claim 1, wherein each of the plurality of ingredients is housed in a respective cartridge of the product dispenser, ingredients of the plurality of ingredients being forced out of the respective cartridge and into the mixing chamber via a force produced from at least one forcing device.

6. The system of claim 5, wherein the at least one forcing device comprises at least one of a motor or a pump.

7. The system of claim 1, wherein the diagnostic device further serves as a toothbrush having bristles for cleaning teeth within the oral cavity.

8. The system of claim 1, wherein the processor is housed in at least one of the diagnostic device, a mobile device, or a server.

9. The system of claim 1, wherein the illumination source is configured to alternately emit the excitation illumination and the scattering illumination during a diagnostic cycle, and wherein the processor is configured to distinguish the fluorescence information from the absorption information based on time periods corresponding to the excitation illumination and the scattering illumination.

10. The system of claim 1, wherein the product expected to remedy the oral condition of the oral cavity is in at least one of a gel, paste, or liquid form factor.

11. The system of claim 1, wherein the illumination source comprises at least one light-emitting diode (LED) configured to emit light in at least one of an ultra-violet, purple, blue, green, red, near-infrared (NIR), or mid-infrared (Mid-IR) spectral range.

12. The system of claim 1, wherein the product dispenser is integrated with a tele-dentistry platform to perform dentist recommended product formulations associated with a treatment regime.

13. A method for diagnosing and treating a condition of an oral cavity, comprising:

alternately illuminating a portion of the oral cavity via a diagnostic device with (i) excitation illumination configured to induce emission fluorescence from the portion of the oral cavity and (ii) scattering illumination configured to produce back scattered light from the portion of the oral cavity, and detecting information relating to emission fluorescence and back scattered light relating to the illuminated portion of the oral cavity, wherein the information comprises fluorescence information and absorption information, the absorption information being derived from the back scattered light;

determining, via at least one of (i) optical data provided via a camera of the diagnostic device or (ii) inertial measurement unit (IMU) data provided via an IMU of the diagnostic device, a location within the oral cavity corresponding to the illuminated portion of the oral cavity;

associating the fluorescence information and the absorption information with the determined location to generate a hygiene map of the oral cavity;

receiving the information relating to the emission fluorescence and the back scattered light, including the fluorescence information and the absorption information;

determining, via a processor, the oral condition of the oral cavity based on the received information relating to the emission fluorescence and the back scattered light;

determining identities of a plurality of ingredients that are expected to remedy the oral condition of the oral cavity based on the hygiene map;

mixing, via a product dispenser, the identified plurality of ingredients thereby producing a product expected to remedy the oral condition of the oral cavity; and dispensing the product expected to remedy the oral condition of the oral cavity via a nozzle of a product dispenser.

14. The method of claim 13, wherein the diagnostic device comprises a camera, the camera comprising at least one of a monochrome camera, bi-chrome camera, red-green-blue (RGB) camera, multispectral camera, hyperspectral camera, or thermal imaging camera.

15. The method of claim 13, wherein each of the plurality of ingredients is housed in a respective cartridge of the product dispenser, ingredients of the plurality of ingredients being forced out of the respective cartridge and into a mixing chamber of the product dispenser via a force produced from at least one forcing device.

16. The method of claim 15, wherein the at least one forcing device comprises at least one of a motor or a pump.

17. The method of claim 13, wherein the diagnostic device further serves as a toothbrush having bristles for cleaning teeth within the oral cavity.

18. The method of claim 13, wherein the processor is housed in at least one of the diagnostic device, a mobile device, or a server.

19. The method of claim 13, wherein the excitation illumination and the scattering illumination are alternately emitted during a diagnostic cycle, and wherein determining the oral condition includes distinguishing the fluorescence information from the absorption information based on time periods corresponding to the excitation illumination and the scattering illumination.

20. The method of claim 13, wherein the diagnostic device comprises at least one light-emitting diode (LED) configured to emit light in at least one of an ultra-violet, purple, blue, green, red, near-infrared (NIR), or mid-infrared (Mid-IR) spectral range.

* * * * *